United States Patent
Pianca et al.

(10) Patent No.: US 7,313,444 B2
(45) Date of Patent: Dec. 25, 2007

(54) SELF-ANCHORING CORONARY SINUS LEAD

(75) Inventors: Anne M. Pianca, Santa Monica, CA (US); Kevin L. Morgan, Simi Valley, CA (US); Gene A. Bornzin, Simi Valley, CA (US); Joseph J. Florio, Bend, OR (US); David J. Vachon, Spokane, WA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 10/081,457

(22) Filed: Feb. 21, 2002

(65) Prior Publication Data

US 2003/0050681 A1 Mar. 13, 2003

Related U.S. Application Data

(63) Continuation of application No. 09/457,277, filed on Dec. 8, 1999, now abandoned, which is a continuation-in-part of application No. 09/196,898, filed on Nov. 20, 1998, now abandoned.

(51) Int. Cl.
*A61N 1/05* (2006.01)
(52) U.S. Cl. ...................................... 607/126

(58) Field of Classification Search ............... 607/119, 607/122, 126–129
See application file for complete search history.

(56) References Cited

U.S. PATENT DOCUMENTS

| | | | |
|---|---|---|---|
| 5,387,233 A * | 2/1995 | Alferness et al. ........... | 607/122 |
| 5,531,781 A | 7/1996 | Alferness et al. ........... | 607/122 |
| 5,683,445 A * | 11/1997 | Swoyer ...................... | 607/119 |
| 5,925,073 A * | 7/1999 | Chastain et al. ............ | 607/122 |
| 6,144,882 A | 11/2000 | Sommer et al. ............ | 607/125 |
| 6,321,123 B1 * | 11/2001 | Morris et al. ............... | 607/122 |
| 6,430,449 B1 * | 8/2002 | Hsu et al. ................... | 607/126 |

* cited by examiner

*Primary Examiner*—George R. Evanisko

(57) ABSTRACT

An implantable cardiac lead system suitable for placement in the coronary sinus region of the heart. The lead system comprises a lead having two or more non-helical bends in its distal portion. The two or more non-helical bends cooperate to prevent the lead from dislodgment or displacement inside the coronary sinus. The lead system may further comprise a stylet suitable for steering the lead into at least one of the coronary sinus vein, great cardiac vein, left marginal vein, left posterior ventricular vein, and small cardiac vein. The stylet is tapered in its distal portion to provide enhanced maneuverability and steerability inside the coronary sinus region. The lead system may also comprise an introducer which aids in introducing the lead into the heart.

19 Claims, 11 Drawing Sheets

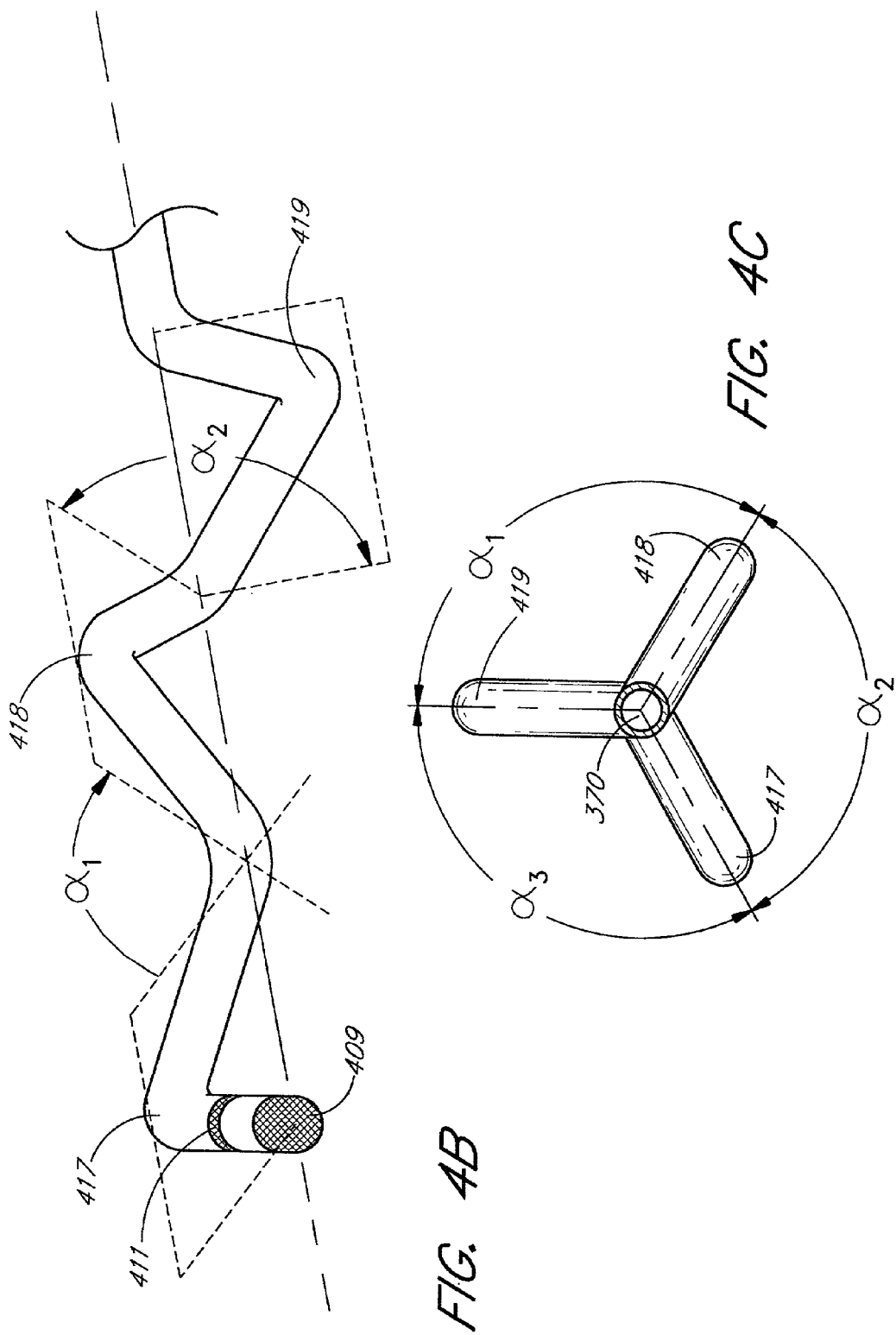

SELF-ANCHORING CORONARY SINUS LEAD

CROSS-REFERENCE TO RELATED APPLICATIONS

This application is a continuation of U.S. patent application Ser. No. 09/457,277, filed Dec. 8, 1999, now abandoned which is a continuation-in-part of U.S. patent application Ser. No. 09/196,898, filed Nov. 20, 1998 now abandoned.

FIELD OF THE INVENTION

The invention relates to implantable stimulation leads. More particularly, the invention relates to an intravenous cardiac lead placed in the coronary sinus and into the vein(s) of the heart to provide pacing of the left atrium and/or left ventricle.

BACKGROUND OF THE INVENTION

To perform cardiac pacing, a lead system is typically positioned in the right chambers of the heart (i.e. right atrium and/or ventricle) through the superior vena cava (SVC). Sometimes, it is desirable to perform sensing, pacing, and/or defibrillation of the left atrium and/or ventricle. However accessing the left chambers of the heart is more difficult than accessing the right chambers of the heart. The left ventricle is a high-pressure chamber which pumps oxygenated blood through the arteries to the furthest extremities of the body. Dislodgment of any portion of the lead located in the left atrium and/or ventricle may result in immediate patient death.

Access to the left chambers of the heart may be achieved through a thoracotomy or transvenous method. Due to the invasiveness and complications associated with a thoracotomy procedure it is desirable to use a transvenous approach.

Several difficulties are associated with placing a lead transvenously to stimulate the left chambers of the heart. Lead placement into the coronary sinus region is often hindered and, sometimes, obstructed by narrow pathways and curvatures. These narrow pathways and curvatures are inherent characteristics of coronary vessels. As used herein, the phrase "coronary sinus" or "coronary sinus region" refers to the coronary sinus vein, great cardiac vein, left marginal vein, left posterior ventricular vein, middle cardiac vein, and/or small cardiac vein or any other cardiac vein accessible by the coronary sinus.

Several attempts have been made to provide a lead, which purports to anchor itself inside a coronary vessel, such as the coronary sinus. One such attempt proposes a lead which includes a coiled configuration and is described in U.S. Pat. No. 5,387,233 issued to Alferness et al. This kind of lead may be vulnerable to several problems when placed into the coronary sinus. In view of its helical structure, this lead may be more difficult to manufacture than ordinary leads. Moreover, the helical end of the lead may not maintain intimate or continuous contact with the inner wall of the vessel. The inability to maintain intimate contact may result from the difficulty of maintaining a geometrically uniform helical structure in the lead. The inability to maintain contact may also be due to inherent anatomical variations of coronary vessels. The lack of contact causes the lead to displace or dislodge from its position inside the vessel. Moreover, the lack of continuous contact with vessel wall makes it difficult to ensure proper contact of electrodes placed in the helical structure with the inner wall of the vessel. Lacking contact by the electrodes with the inner wall of the vessel renders cardiac stimulation ineffective or sensing inaccurate.

Hence, as noted above, adequate fixation of the lead and electrode in a coronary vessel is difficult to achieve. Like the posterior vein of the left ventricle, distal coronary vessel tributaries have small diameters. The leads placed in these vessels should track well and have a small diameter so they may be placed in distal vessels. The electrode should have intimate contact with the tissue and it should not dislodge. A small electrode, less than the diameter of the vessel, is likely to move easily within the vessel and may not be adequately affixed which results in displacement or dislodgment of the lead.

Thus, there is a need in cardiac pacing technology to be able to introduce and place a lead having one or more electrodes in regions of the heart having narrow pathways and variable curvatures. The lead should accommodate for placement in the coronary sinus region without experiencing displacement or dislodgment.

SUMMARY OF THE INVENTION

The invention provides a lead, which may be securely affixed in the coronary sinus region. The lead is formed to have at least two bends. This is accomplished by preforming the tubing (i.e., insulation layer) and/or the winding (i.e., conductor coil) into the desired configuration. At least one electrode is placed on, before, or after the outer curve of the at least two bends in the distal portion of the lead. During insertion of the lead, a stylet is placed through a lumen in the lead. Alternatively, the lead may be slid over a guidewire. The stylet or guidewire straightens the at least two bends to facilitate handling of the lead. When the appropriate location for the lead is found, the stylet or guidewire is removed and the bend configuration is restored. The lead is secured into position due to the bend, which exerts pressure against the inner walls of the vessel to maintain position.

Another aspect of the invention relates to electrode configuration. Two electrodes provide for bipolar pacing and sensing. The benefits of the bipolar configuration are well known. In addition to the tip electrode at the distal end of the lead, at least one ring electrode may be place anywhere proximal to the distal tip electrode. That is, a ring electrode may be placed on, before, or after the curve of either one of the two bends. In the preferred embodiment, the ring electrode is placed on the straight portions, either before or after the bends so that a stylet can more easily traverse the bends. Thus, the electrodes may be located in the same geometric plane and oriented approximately 180 degrees apart. The coronary veins are located on the surface of the epicardium. The inside wall of the vein is adjacent to the myocardium and the outside wall of the vein is adjacent to the pericardium. Only the myocardium is excitable. Consequently, placement of electrodes may be forgiving if one electrode is oriented toward the pericardium and the other electrode is oriented toward the myocardium. Thus, at least one electrode may be capable of performing low threshold stimulation.

Another feature of the design allows for placement of the lead over a guidewire. A guidewire may be placed in the coronary sinus using a catheter, such as the 7F CSL catheter manufactured by DAIG. Once the CSL catheter is in position, a guidewire may be advanced through the catheter. The guidewire may be selectively positioned into the coronary sinus.

The guidewire may be insulated to the tip to allow pacing through the guidewire and support mapping, including hemodynamic mapping. During hemodynamic mapping, cardiac performance is assessed using blood pressure, contractility, or cardiac output. Optimal placement of a catheter may be determined by hemodynamic monitoring and a pacing guidewire may aide in this process. Finally, once the guidewire is positioned, the CSL catheter may be carefully slide off the guidewire leaving the guidewire in position. The pacing lead may then be placed over the guidewire and positioned deep in a cardiac vein.

Placing the lead with a guidewire may not be necessary if the lead is placed with a steerable stylet. The lead is steerable when it is placed using a stylet instead of a guidewire. When the stylet is inserted, the lead is substantially straight. When the stylet is withdrawn, the preformed most distal bend cants at least part of the distal portion of the lead. This cant makes the distal portion steerable. Varying the degree of bias is a characteristics that is consistent with steerable catheters.

In one embodiment, the lead system comprises at least one electrode configured to perform at least one of sensing, pacing, cardioversion, and defibrillation of the heart. The lead system further comprises a lead connected to the at least one electrode. The lead includes a distal portion having at least two non-helical bends dimensioned to passively anchor the lead in the coronary sinus. In another embodiment, the lead system comprises a lead which includes a distal portion having first and second bends located in the same geometric plane. The first and second bends are configured to passively anchor the lead inside the coronary sinus. The lead system further comprises a first electrode positioned at the tip of the lead, and a second electrode positioned between the first bend and the tip of the lead.

In another embodiment, the lead system comprises means for delivering signals between a cardiac device and the heart. The delivery means includes a distal portion having at least two non-helical bends dimensioned for passively anchoring the delivery means inside the coronary sinus. The lead system further comprises means, connected to the distal portion, for stimulating the heart. The stimulation means are configured for performing at least one of sensing, pacing, cardioversion, and defibrillation of the heart. In another embodiment, the lead system comprises means for delivering signals between a cardiac device and the heart. The delivery means includes a co-planar distal portion configured for passively anchoring the delivery means inside the coronary sinus. The lead system further comprises first and second means for stimulating the coronary sinus positioned at the co-planar distal portion.

The invention further provides a method of making a lead for placement in the coronary sinus. The method comprises the step of shaping an insulation layer to surround a lumen so as to form at least two non-helical bends, which are dimensioned to passively anchor the lead in the coronary sinus. The method further comprises the step of placing at least one conductor inside the lumen.

BRIEF DESCRIPTION OF THE DRAWINGS

The above and other aspects, features and advantages of the invention will be better understood by referring to the following detailed description, which should be read in conjunction with the accompanying drawings, in which:

FIG. 4B is a perspective view of the lead of FIG. 4A.

FIG. 4C is a cross-sectional view of the lead of FIG. 4A taken at 4C of FIG. 4A.

DETAILED DESCRIPTION OF THE INVENTION

The following description is not to be taken in a limiting sense, but is made merely for the purpose of describing the general principles of the invention. The scope of the invention should be determined with reference to the claims.

Figure 1:
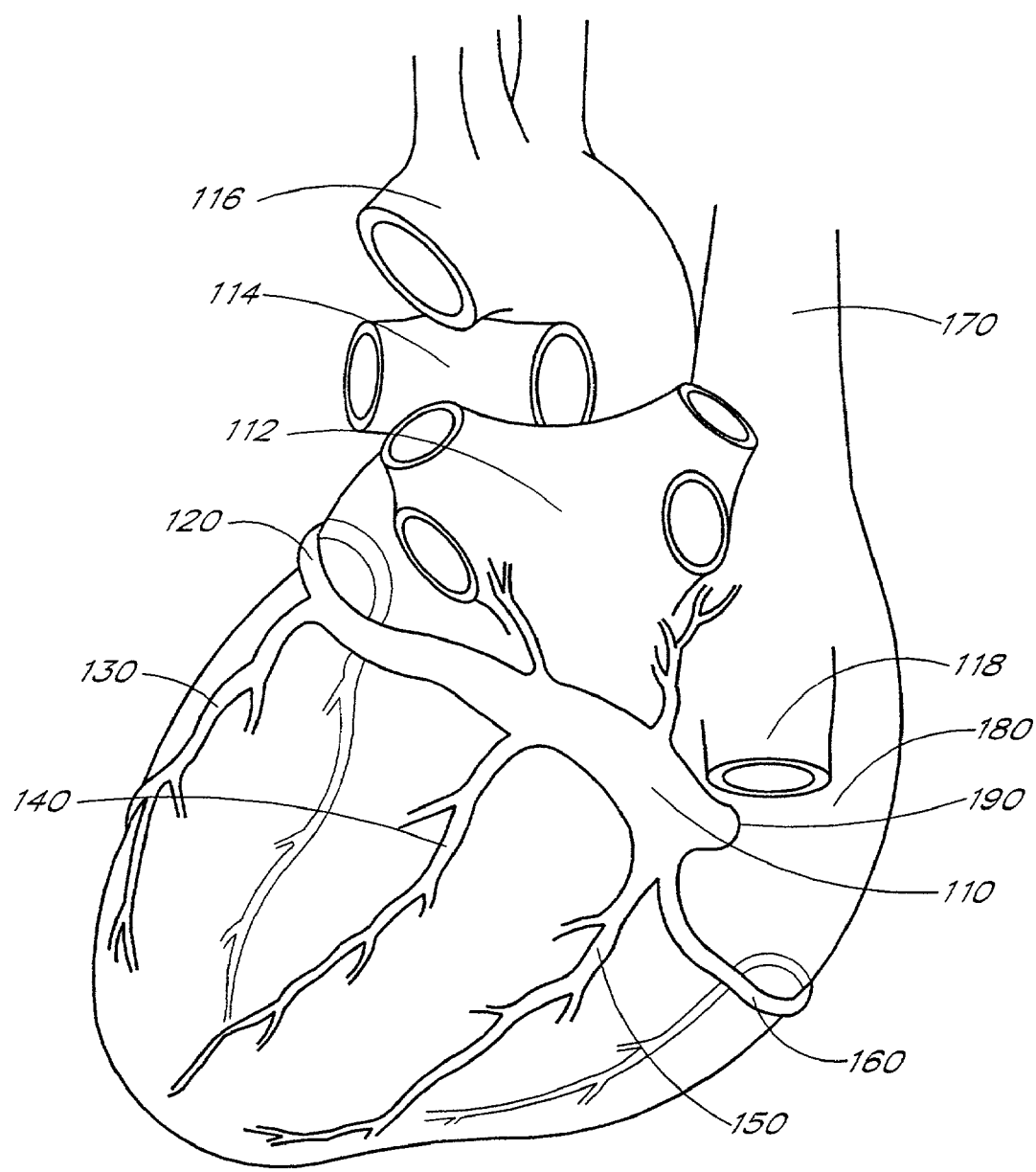
FIG. 1 is a perspective view of the left-posterior region of the heart.

As indicated above, the invention provides an implantable lead system for placement in difficult-to-reach regions of the heart. To better understand the details of the invention, an overview of the relevant anatomy of the coronary sinus region of the heart is first provided. FIG. 1 is a perspective view of the left-posterior region of the heart 100. As shown in FIG. 1, the coronary sinus vein 110 is the main vein of the heart. Typically, the coronary sinus vein 110 is a venous channel of about 2 centimeters in length which runs from right to left in the posterior part of the coronary groove. The coronary sinus vein 110 connects to the great cardiac vein 120 at its left end. Moreover, the coronary sinus vein 110 connects to the left marginal vein 130 and left posterior ventricular (LPV) vein 140 in its middle region. The coronary sinus vein 110 also connects to the middle cardiac vein 150 and small cardiac vein 160 at its right end. The coronary sinus vein 110 opens into the right atrium 180 through an ostium or os 190. Finally, the arch of aorta 116, pulmonary arteries 114, pulmonary veins 112, and inferior vena cava (IVC) 118 are also shown in FIG. 1.

Figure 2:
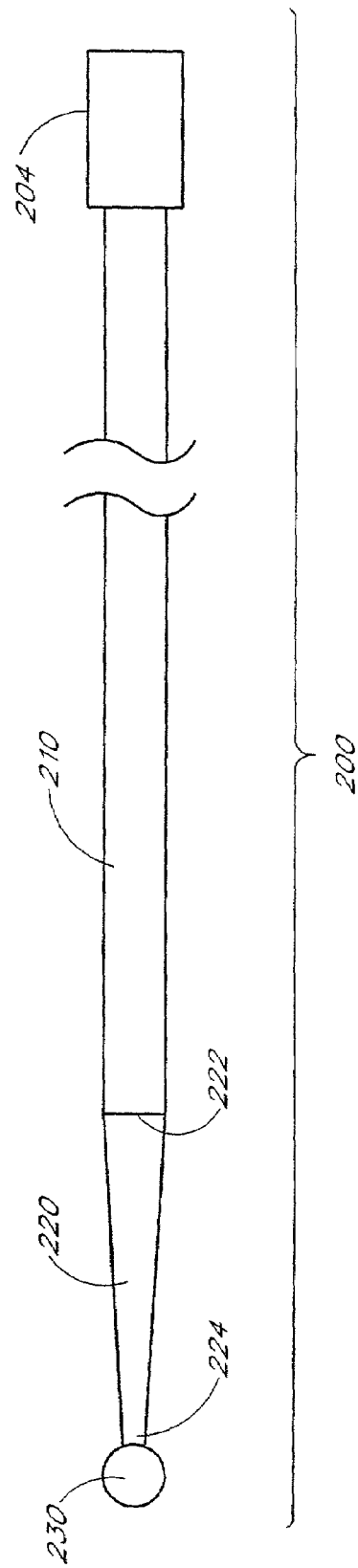
FIG. 2 is a longitudinal view of one embodiment of the stylet of the invention.

FIG. 2 is a longitudinal view of one embodiment of the stylet of the invention. As shown in FIG. 2, the stylet 200 comprises a main body 210 connected to a tapered portion 220 on one side, and is connected to a knob 204 on another side. The knob 204 aids in handling and identifying the stylet 200. At its distal portion, the tapered portion 220 is connected to a spherical portion 230, which aids to prevent perforation of the lead insulation layer and subsequently the vessel during implantation of the lead. The tapered portion 220 aids in maneuvering and steering the lead during implantation into difficult-to-reach heart regions, such as the coronary sinus region. Additionally, the tapered portion 220 aids in tracking coronary sinus vessels and manipulating the lead.

The stylet 200 is typically made of 304 stainless steel. The stylet 200 may be adapted to a variety of shapes and sizes, which are suitable for insertion into the coronary sinus region. The length of the main body 210 varies depending on the particular implantation configuration and the length of the lead. Typically, the length of the main body 210 may be about 30 inches. However, a length of 25-35 inches may also be suitable for the main body 210. The main body 210 may have a substantially invariant diameter 212 (or maximum cross-distance in case of non-cylindrical shapes) in the range of about 0.003-0.015 inches. More preferably, the diameter 212 of the main body 210 may be about 0.014 inches. The length of the tapered portion 220 may be in the range of about 0.8-5 inches. More preferably, the length of the tapered portion 220 may be about 2 inches.

As shown in FIG. 2, in one embodiment the tapered portion 220 may have a conical shape with a wide end 222 and narrow end 224. The tapered portion 220 may have any geometric shape such as a pyramidal, hexagonal, donut, elliptical, triangular, rectangular, or other similar shape suitable for insertion in the heart. The diameter of the wide end 222 is substantially equal to the diameter of the main body 210. Hence, the diameter of the wide end 222 may be in the range of about 0.003-0.015 inches. More preferably, the diameter of the wide end 222 may be about 0.014 inches. The diameter of the narrow end 224 may be in the range of about 0.003-0.011 inches. More preferably, the diameter of the narrow end 224 may be about 0.010, 0.008, 0.006, 0.005, or 0.004 inches. Consequently, the ratio of the diameters of the wide end 222 to the distal portion 224 is about 1.3 or more. Moreover, the ratio of the length of the tapered portion 220 to the diameter of the wide end 222 is about 50 or more. The ratio of the length of the tapered portion 220 to the diameter of the narrow end 224 is about 70 or more. Finally, the diameter of the spherical portion 230 may be about 0.008-0.015 inches. More preferably, the diameter of the spherical portion 230 may be about 0.014 inches.

The tapered characteristic of the stylet 200 allows for trackability inside distal and narrow coronary vessels. It is desirable to have the main body 210 be stiffer than the tapered portion 220. The difference in stiffness allows for bending and flexing of the tapered portion 220 while maintaining a substantially straight main body 210. This kind of stiffness characteristic aids in curving and steering the spherical portion 230 into a coronary vessel having tortuous angle of entry into the coronary vessel (e.g., LPV).

Figure 3A:
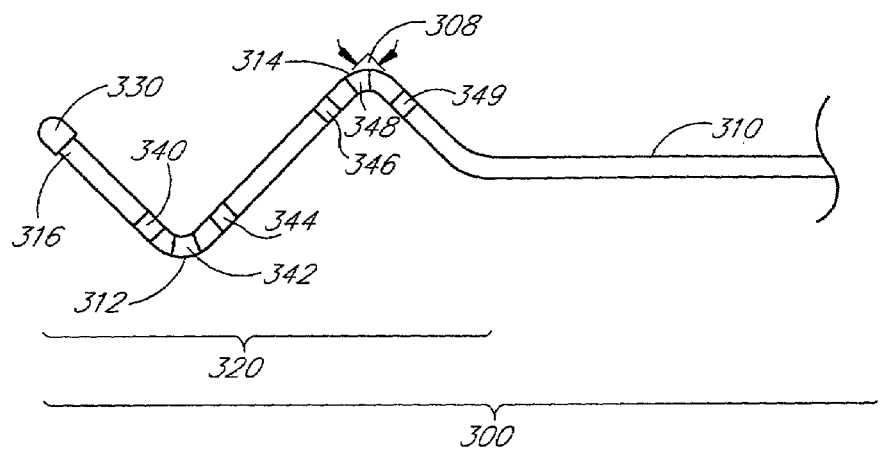
FIG. 3A is a side view of a first embodiment of the lead of the invention.

FIG. 3A is a side view of one embodiment of the lead of the invention. The lead 300 comprises a main body 310 connected to a distal portion 320 having one or more electrodes. The distal portion 320 represents the portion of the lead 300 which proximally extends from a distal tip 316 up to a length of about 1-4 inches. The distal portion 320 is configured to have two or more bends (also called "humps"). As used herein, a bend comprises a location of intersection of two sides of the lead, excluding locations of intersection, which are co-linear with the geometric line passing through the main body 310. The angle 308 formed by the two sides may be in the range of about 30-150 degrees.

In this embodiment, the distal portion 320 has a first bend 312 and a second bend 314. The first bend 312 is formed in a region located opposite to, and in the same geometric plane as (i.e., co-planar with), the region where the second bend 312 is formed. However, each bend does not have to be located in such a configuration in relation to the other one or more bends. More particularly, the first bend 312 and second bend 314 may lie in a separate geometric plane, be formed in opposite regions, or be formed in the same region. The distance between the first bend 312 and the tip 316 may be in the range of 0.15-0.7 inches. The distance between the first bend 312 and second bend 314 may be in the range of 0.15-0.7 inches. The distance between the first bend 312 and second bend 314 may be measured between the centers of the two bends, or between any consistent or equivalent locations on the two bends.

As shown in FIG. 3A, the distal portion 320 includes a first electrode 330 as a tip electrode. A second electrode is shown placed between the tip 316 and the first bend 312, and identified as ring electrode 340. Alternatively, the second electrode may be a ring electrode 342 placed on the first bend 312, or a ring electrode 344 between the first bend 312 and second bend 314, or a ring electrode 346 before the second bend 314, or a ring electrode 348 on the second bend 314, or a ring electrode 349 after the second bend 314. In the preferred embodiment, the second electrode is placed on the straight portions, either before or after the bends, 312 or 314, so that a stylet can more easily traverse the bends.

As shown in FIG. 3A, the distal portion 320 includes a first electrode 330 as a tip electrode, and a second electrode 340 as a ring electrode. The second electrode 340 is placed between the tip 316 and the first bend 312. Alternatively, the second electrode 340 may be placed on the first bend 312, between the first bend 312 and second bend 314, on the second bend 314, or before the second bend 314. It is desirable to have the distance between the first electrode 330 and second electrode 340 be in the range of 0.15-0.6 inches and, particularly, 0.30 inches. It is desirable, however, to have the distance between these electrodes be sufficient to allow the first electrode 330 and the second electrode 340 to be placed in the LPV vein 140. The placement of electrodes in this arrangement ensures achieving capture of the left ventricle. Capture may be defined as the successful depolarization and contraction of a cardiac chamber (e.g., atrium or ventricle) in response to a stimulation pulse generated by an implantable device, such as a pacemaker or ICD.

The invention may employ other electrode configurations and still maintain the spirit of the invention. For example, one electrode configuration may include the use of two ring electrodes, one located at the first bend 312 and the other at the second bend 314. Another electrode configuration may include using a tip electrode 330 to perform unipolar sensing, pacing and/or cardioversion-defibrillation. The kind of electrode configuration used depends on the particular application. Hence, other electrode configurations, which are known in the art, may also be used. With the selected configuration, an implantable cardiac device, such as a pacemaker or ICD (not shown in this figure), may be connected to the first electrode 330 and second electrode 340 to perform bipolar sensing, pacing and/or cardioversion-defibrillation to the left ventricle through the coronary sinus region.

Figure 3B:
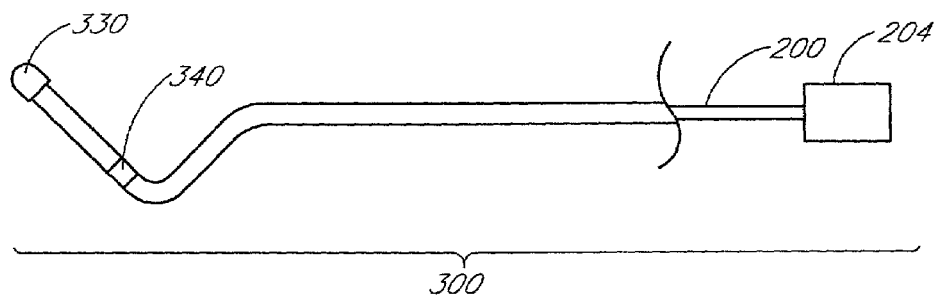
FIG. 3B is a side view of the lead of FIG. 3A having the stylet of FIG. 2 partially inserted therein.

In view of the flexibility of its material, the lead 300 may be implanted in its destination using a stylet. Accordingly, to implant and position the lead 300 in a patient's heart, the stylet 200 is typically inserted into a lumen 370 (see FIG. 3D) inside the lead 300 to guide, steer, and maneuver the lead 300 into a desired region in the heart 100. FIG. 3B is a side view of the lead of FIG. 3A when the stylet 200 is partially inserted therein. As shown in FIG. 3B, when the stylet 200 is partially inserted into the lead 300, up to the second bend 314, the lead 300 is straightened out, so as to be in substantial alignment with the unbent portion of the lead 300. The lead 300 changes its shape to conform with the straight shape of the stylet 200. However, the lead 300 and stylet 200 remain sufficiently flexible and steerable for placement in difficult regions of the heart 100, such as the coronary sinus region.

Figure 3C:
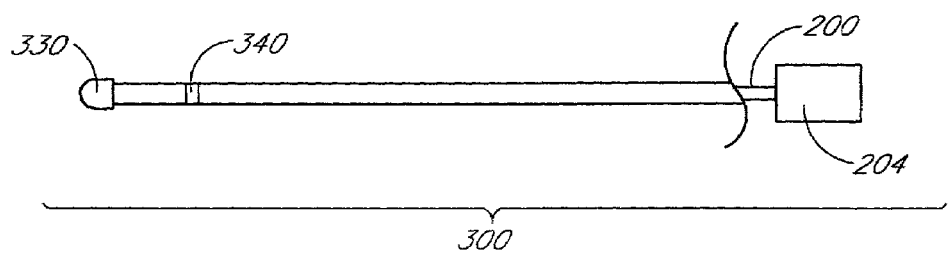
FIG. 3C is a side view of the lead of FIG. 3A having the stylet of FIG. 2 substantially fully inserted therein.

FIG. 3C is a side view of the lead of FIG. 3A when the stylet 200 is substantially fully inserted therein. As shown in FIG. 3C, when the stylet 200 is fully inserted inside the lead 300, the lead 300 is completely straightened out in conformance with the shape of the stylet 200. Typically, the lead 300 is fully inserted with the stylet 200 before implantation into the heart 100. As the stylet 200 bends and curves in the course of implantation, the lead 300 bends and curves with the stylet 200. Once the lead 300 reaches its intended position, the stylet 200 is withdrawn from the lead 300. After withdrawal of the stylet 200, the lead 300 regains its original shape and, particularly, the first bend 312 and second bend 314 reappear as shown in FIG. 3A.

The presence of the first bend 312 and second bend 314 aids in keeping the lead 300 in its place after withdrawing the stylet 200 from the lead 300. When the lead 300 is in its position inside a vessel, at least a portion of the first bend 312 is in contact with a portion of the inner surface of the vessel. Moreover, at least a portion of the second bend 314 is in contact with another portion of the inner surface of the vessel. In this embodiment, the two portions of the inner surface of the vessel contacted by the bends 312 and 314 are typically on opposite sides of the vessel. Contact between the bends and the inner wall of the vessel creates opposite friction forces (also called "bias"). This bias prevents the lead 300 from displacement or dislodgment, thereby causing the lead 300 to self-anchor in its position.

Figure 3D:
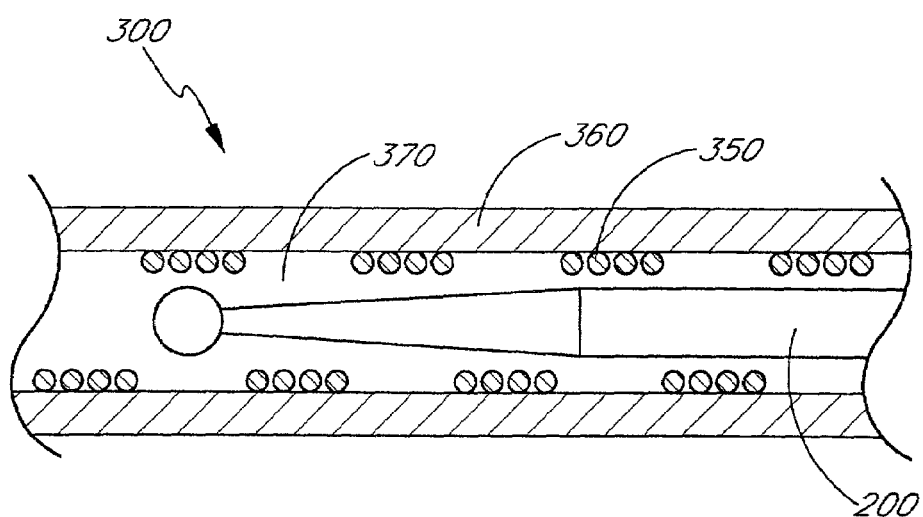
FIG. 3D is a cross-sectional view taken along the length of the lead of FIG. 3C having the stylet of FIG. 2 inserted therein.

FIG. 3D is a cross-sectional view taken along the length of the lead 300 having the stylet 200 inserted therein. As shown in FIG. 3D, the lead 300 comprises one or more conductor coils 350 surrounded by a layer of insulation material 360. The conductor coil 350 may be made of any electrically conductive material such as MP35N, or other conductive material, which is known in the art. The conductor coil 350 is inserted into the lumen 370 so that a guidewire or stylet 200 may to pass therethrough. The insulation 360 may comprise any flexible and implantable material, such as silicone, polyurethane, or other similar material, which is suitable for implantation inside a human body. The lead 300 carries output stimulus signals from a pulse generator to the heart 100 and, in demand mode, relays intrinsic cardiac signals back to a sensing circuit. More particularly, the conductor coil 350 allows current to flow between the pacemaker and the heart 100.

The following method may be applied to make and shape the lead 300 with the two or more bends as shown in FIGS. 3A-3D. As noted above, the insulation 360 may comprise any flexible implantable material, such as silicone or polyurethane. In one embodiment, the material of the insulation layer 360 comprises silicone. The silicone may comprise the medical grade Q7-4780 rubber manufactured by Dow Corning. The silicone is first extruded at about room temperature (i.e., 25 degrees centigrade). Substantially immediately thereafter, the silicone is passed through a heater or oven having a temperature of about 370 degrees centigrade for a period of few seconds (e.g., 2-20 seconds). Passing the silicone through the oven partially cures and sets the silicone. The partially cured silicone is placed in a shaped fixture having a desired shape and, particularly, number of bends (e.g., two or more bends). The fixture is placed with the silicone in a heater or oven having a temperature in the range of about 115-150 degrees centigrade, until fully cured. Typically, the silicone is fully cured after a period of about 2 hours.

Once fully cured, the silicone tubing (i.e., insulation 360) is cooled down to about room temperature to retain the desired shape substantially permanently. Once the silicone is cooled down, the insulation 360 retains its flexible and resilient characteristics. More particularly, the silicone retains the two or more bends in the distal portion 320. Thereafter, one or more conductor coils 350 may be inserted inside the lumen 370. Additionally, one or more electrodes may be positioned in the distal portion 320 as described in FIGS. 3A-3D.

In another embodiment, the material of the insulation 360 comprises polyurethane. The polyurethane may comprise Pellethane 80A or 55D. When using polyurethane to prepare the lead 300, steps similar to those described above may be followed. However, the temperature of the heater or oven used to set the polyurethane is above the glass transition temperature, which is about 70 degrees centigrade. Additionally, in view of its thermoplastic properties, the polyurethane insulation 360 may be re-shaped after extrusion. More particularly, if desired, the polyurethane insulation 360 may be re-shaped into a different form, or another number of bends, by heating the polyurethane again to above about 70 degrees centigrade. Hence, re-shaping the polyurethane is still possible after curing. In some circumstances, the thermoplastic property of polyurethane may prove quite effective in manufacturing the lead 300.

In implementing either of the foregoing methods to prepare the insulation 360, one or more conductor coils 350 are inserted inside the lumen 370 without distorting or interfering with the molded shape of the two or more bends in the distal portion 320. More particularly, when the insulation 360 forms and sustains the two or more bends in the distal portion 320, it is not necessary to introduce independent bends in the shape the conductor coil 350. Typically, the shape and material making up the conductor coil 350 render the conductor coil 350 sufficiently flexible to conform to the shape of the insulation 360.

Alternatively, one skilled in the art may desire to select the conductor coil 350 to form and sustain the two or more bends in the distal portion 320. If so, the insulation 360 may optionally be shaped without the two or more bends in the distal portion 320 so that, upon insertion of the conductor coil 350 into the lumen 370, the insulation 360 conforms to the shape of the conductor coil 350 having the two or more bends.

Figure 4A:
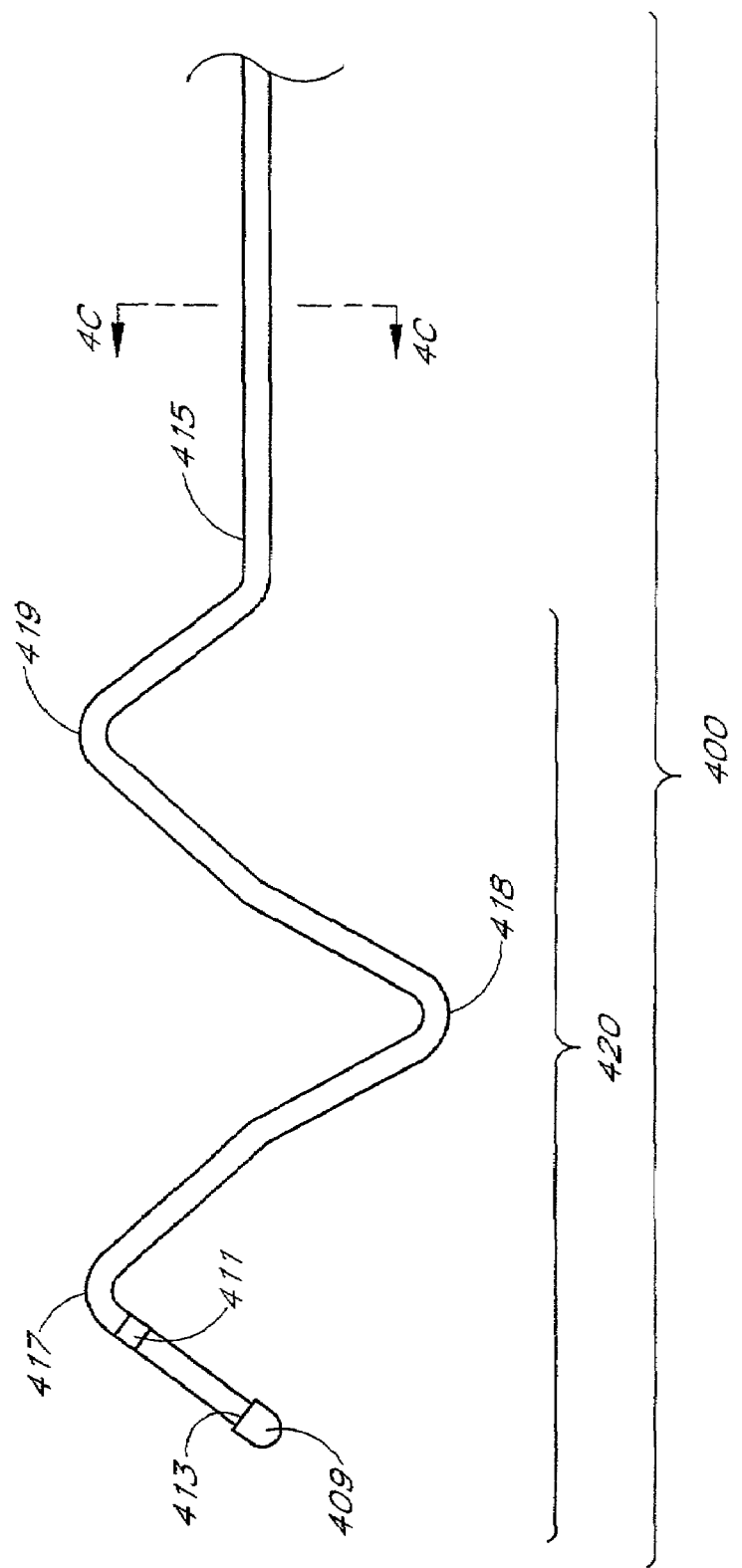
FIG. 4A is a side view of a second embodiment of the lead of the invention.

FIG. 4A shows a lead 400 comprising at least three bends in a distal portion 420. The lead 400 comprises a flexible body 415 connected to the distal portion 420, having one or more electrodes. In this embodiment, the distal portion 420 has a first bend 417, second bend 418, and third bend 419. Each bend is located in a unique geometric plane. In this embodiment, each unique geometric plane forms an angle of, for example, 120 degrees with the other unique geometric plane. However, each bend does not have to be located in such a configuration in relation to the other one or more bends. More particularly, the first bend 417, second bend 418, and third bend 419 may all lie in the same geometric plane. The distance between the tip 413 and first bend 417 may be in the range of about 0.15-0.6 inches. The distance between each two adjacent bends may be in the range of about 0.15-0.7 inches. The distance between each two bends may be measured between the centers of the two bends, or between any consistent or equivalent locations on the two bends.

In all other respects, characteristics of the lead 400 are similar to those of the lead 300 including, among other things, flexibility of the bends which is illustrated in FIGS. 3A-3D. Moreover, the distal portion 420 comprises a first electrode 409 as a tip electrode, and a second electrode 411 as a ring electrode. The second electrode 411 may be placed between the tip 413 and the first bend 418. Alternatively, the second electrode 411 may be placed on the first bend 417, between the first bend 417 and second bend 418, on the second bend 418, between the second bend 418 and third bend 419, on the third bend 419, or before the third bend 419.

FIG. 4B is a perspective view of the lead 400. As shown in FIG. 4B, each of the three bends 417, 418, and 419 is located in a unique geometric plane. As noted above, each unique geometric plane forms an angle of, for example, 120 degrees with the other unique geometric plane. However, each of the three bends 417, 418, and 419 does not have to be located in such a configuration in relation to the other one or more bends. More particularly, the first bend 417, second bend 418, and third bend 419 may all lie in the same geometric plane. Moreover, the angles (i.e., $\alpha_1$, $\alpha_2$ and $\alpha_3$) between two unique geometric plane may have any desirable value, i.e., in the range of about 0-180 degrees.

FIG. 4C is a cross-sectional view of the lead 400 taken at 4C of FIG. 4A and having a viewing direction towards the tip 413. As shown in FIG. 4C, the projection of the three bends 417, 418, and 419 extend outward away from the lumen 470. Moreover, as noted above, each of the three bends 417, 418, and 419 is located in a unique geometric plane, and each unique geometric plane forms an angle of, for example, 120 degrees with the other unique geometric plane.

Figure 5:
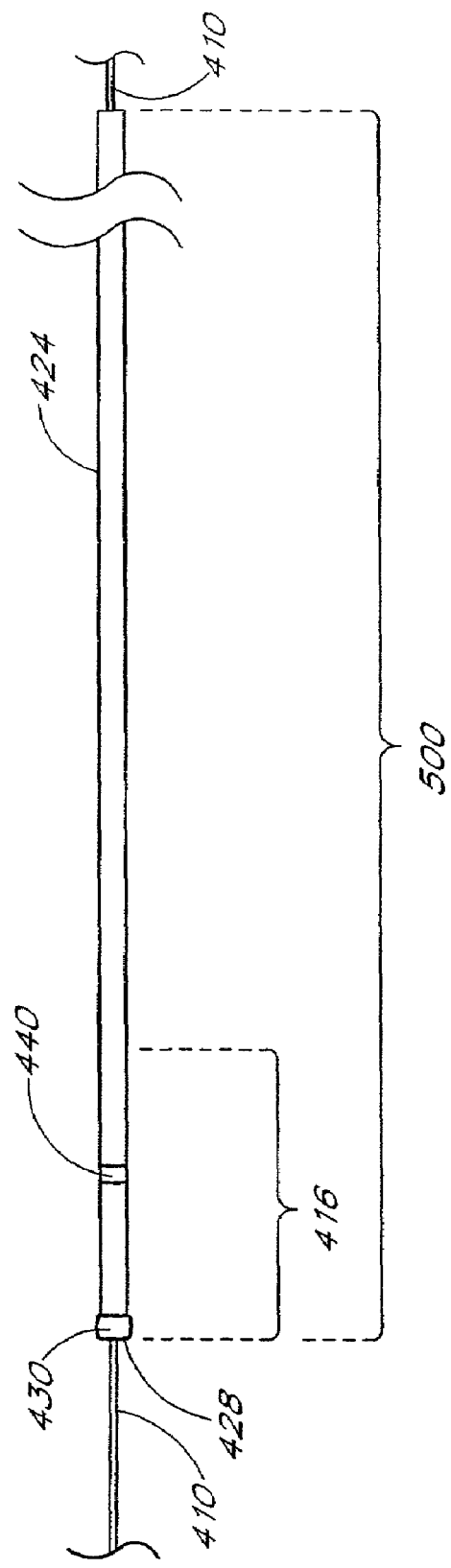
FIG. 5 is a side view of a third embodiment of the lead of the invention having a guidewire substantially fully inserted therein.
Figure 8:
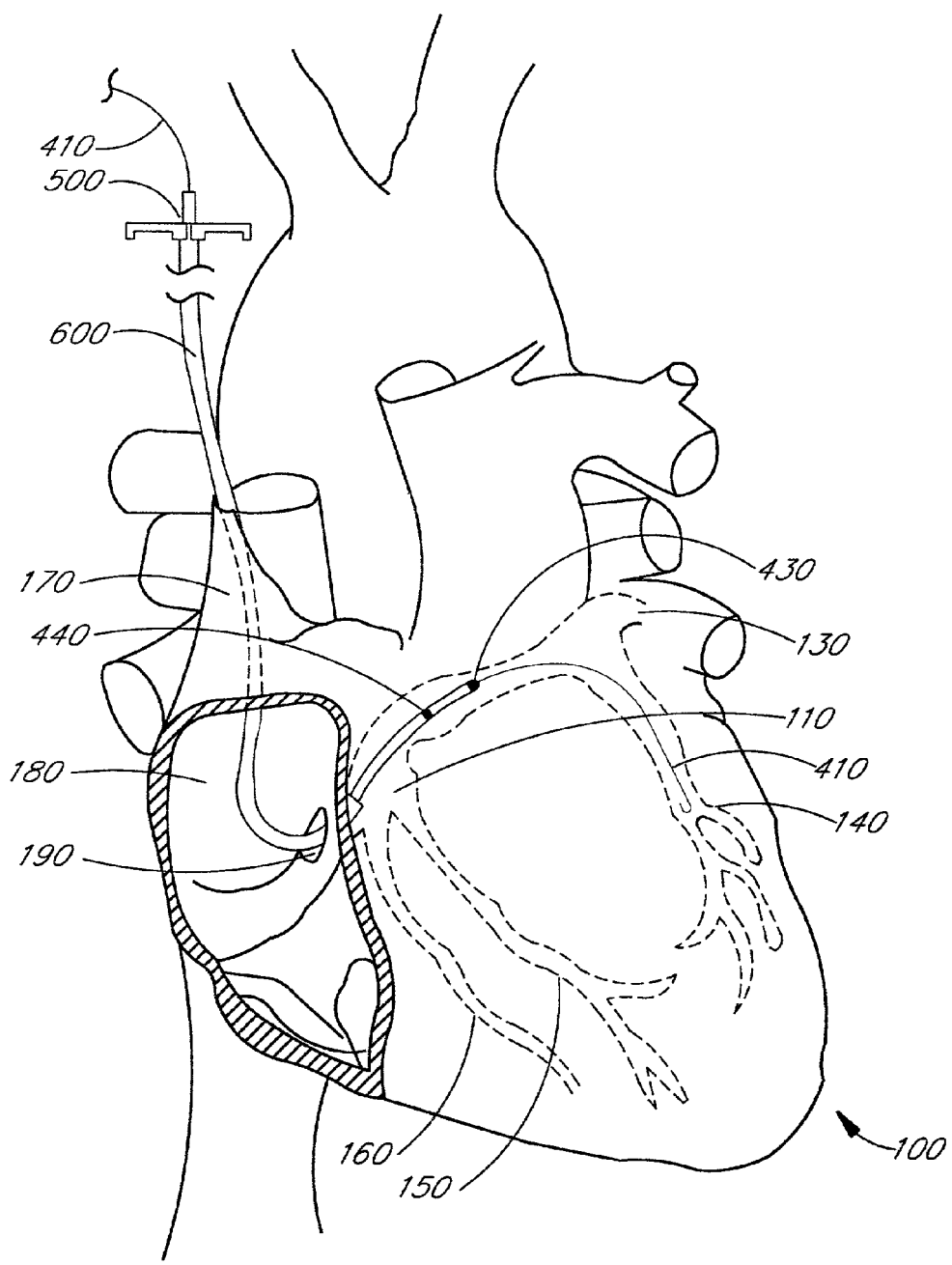
FIG. 8 is a perspective view of the anterior portion of the heart showing the coronary sinus region having the lead system of FIG. 5 inserted therein.

FIG. 5 is a side view of a lead 500 having a guidewire 410 substantially fully inserted therein. The lead 500 comprises a main body 424 connected to a distal portion 416 having an opening 428. In all other respects, characteristics of the lead 500 are similar to those of the lead 300 including, among other things, two or more bends which are described in FIGS. 3A-3D. Typically, the lead 500 slides over the guidewire 410 by allowing the guidewire 410 to be fully inserted into the opening 428 and extending out of the main body 424. The diameter of the opening 428 may be in the range of about 0.020-0.060 inches. In view of the open distal portion 416, the guidewire 410 may be used to guide the lead 500 as illustrated in FIG. 8. If desired, an electrode 430 suitable for placement on the distal portion 416, such as a ring electrode, may be placed on the distal portion 416. Moreover, one or more ring electrodes (e.g., a ring electrode 440) may be placed on, before, or after one or more bends as described for the lead 300.

Figure 6A:
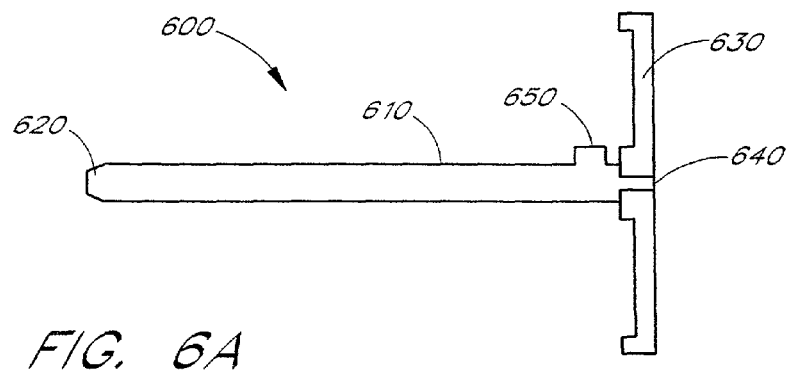
FIG. 6A is a side view of one embodiment of an introducer sheath in accordance with the invention.

FIG. 6A is a side view of one embodiment of an improved introducer sheath 600 in accordance with the invention. The introducer sheath 600 comprises a main body 610 connected to a tapered portion 620 on one end, and connected to a handle 630 on the other end. Additionally, the introducer sheath 600 comprises a first port 640 extending from the handle 630 to the main body 610. The first port 640 allows one or more objects to be inserted into the main body 610 through the handle 630. The first port 640 may be cylindrical in shape having a diameter in the range of 7-11 F (i.e., 0.23-0.37 centimeters). The introducer sheath 600 may optionally comprise a second port 650 connected to one side of the main body 610. The second port 650 may be a flexible cylindrical duct having a diameter of about 7-11 F (i.e., 0.23-0.37 centimeters). The second port 650 allows substance such as liquids or dyes to be poured into the main body 610 without having to go through the first port 640.

Figure 7:
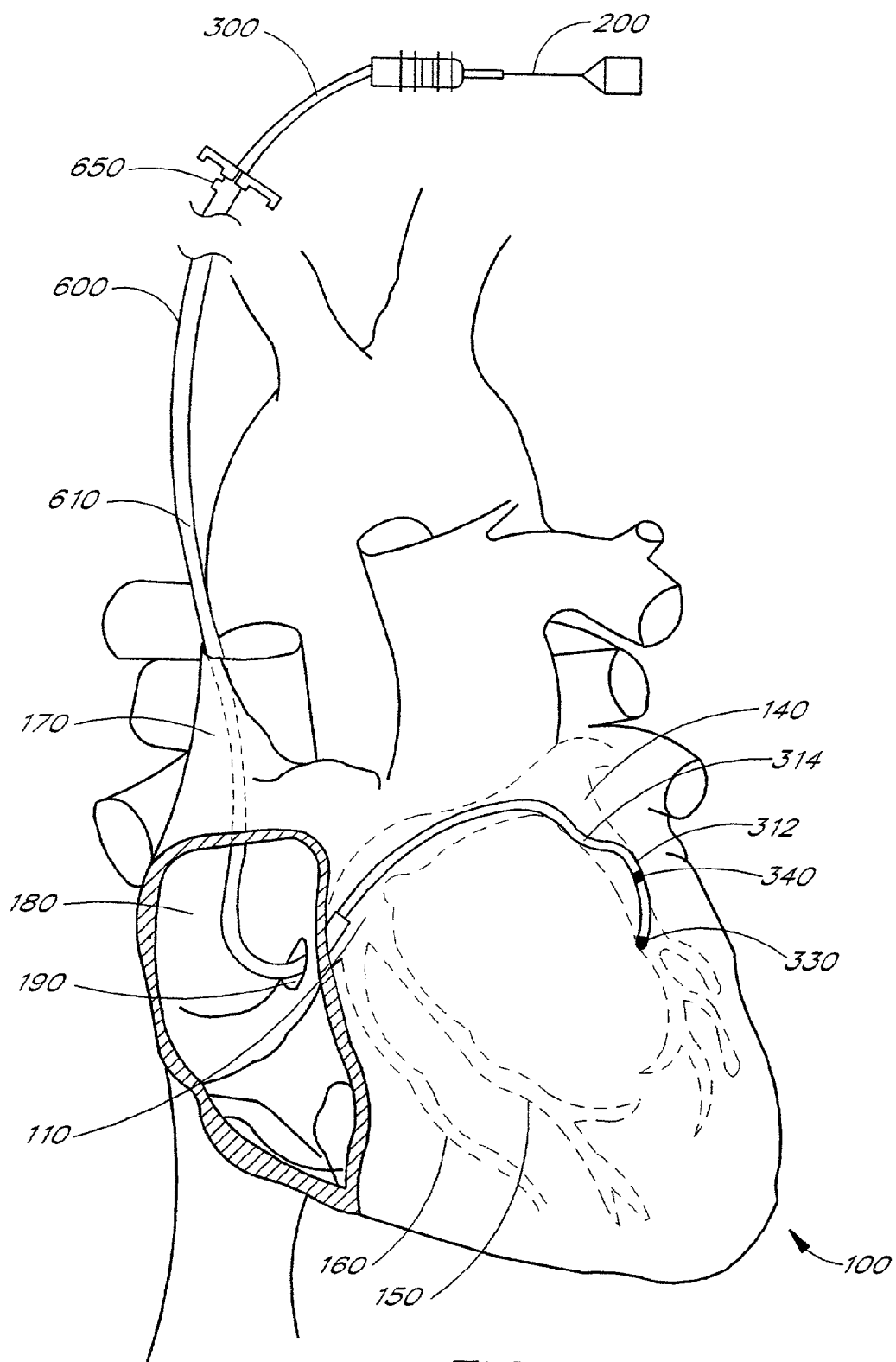
FIG. 7 is a perspective view of the anterior portion of the heart showing the coronary sinus region having the lead system of FIG. 3C inserted therein.

Advantageously, the introducer 600 of the present invention is longer (about 45 cm) than conventional introducers so that the distal end of the introducer 600 reaches the os. The introducer may further be configured to curve past the os (as shown in FIG. 7), either by constructing the distal end of the introducer to be flexible enough for the guidewire to guide the introducer into the os, or by pre-shaping the distal end of the introducer.

The introducer sheath 600 may optionally comprise a second port 650 connected to one side of the main body 610. The second port 650 may be a flexible cylindrical port typically fitted with a luer lock (not shown). The second port 650 allows substance such as liquids or dyes to be injected into the main body 610.

Typically, the main body 610 is a hollow cylinder having an inner diameter of about 9 F (i.e., 0.3 cm). However, the diameter of the main body 610 may alternatively be in the range of about 6-11 F (i.e., 0.23-0.37 cm). The length of the main body 610 may be in the range of about 35-70 cm. The tapered portion 620 is substantially conical in shape having a small diameter and a large diameter. The small inner diameter of the tapered portion 620 is 7-11 F), and the small inner diameter is typically in the range of about 4-7-11 F. The introducer sheath 600 may be made of any biocompatible material, such as polyethylene.

Figure 6B:
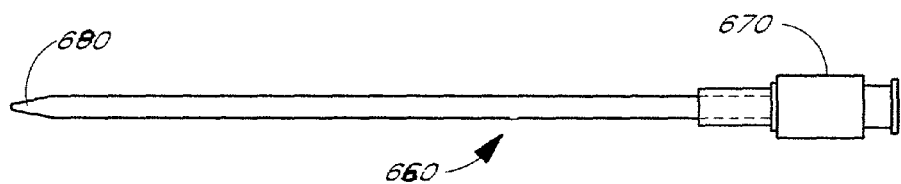
FIG. 6B is a side view of a guiding rod in accordance with the invention.

FIG. 6B is a side view of the dilator 660 in accordance with the invention. The dilator 660 is typically a hollow cylinder comprising a tapered portion 680 and a knob 670. It is desirable to have the dilator 660 be stiffer than the introducer sheath 600. The invariant diameter of the dilator 660 may be in the range of about 6-11 F. The length of the dilator 660 may be in the range of about 40-75 cm.

The tapered portion 680 comprises a small diameter and a large diameter. The large diameter of the tapered portion 680 is 7-14 F. The small diameter of the tapered portion 680 is in the range of about 3-7 F (i.e., 0.07-0.23 cm). The length of the tapered portion 680 may be in the range of about 0.3-1.5 cm. The knob 670 allows a clinician to handle the dilator 660 during insertion into or removal from the introducer sheath 600.

The introducer sheath 600 may alternatively be selected to be a peel-away introducer, such as the 9F Peel-Away Introducer manufactured by DAIG® Corporation. The introducer sheath 600 may include a locking dilator, such as Di-Lock™ manufactured by DAIG® Corporation. Any other introducer, which is suitable for insertion of the lead 300 may also be used.

Figure 6C:
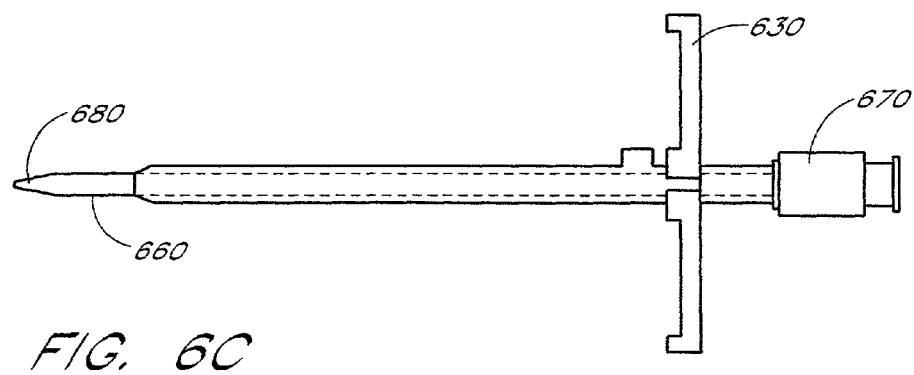
FIG. 6C is a side view of the introducer sheath of FIG. 6A with the guiding rod of FIG. 6B substantially fully inserted therein.

FIG. 6C is a side view of the introducer sheath 600 with a dilator 660 substantially fully inserted therein. As shown in FIG. 6C, the dilator 660 is inserted into the introducer sheath 600 to provide or increase stiffness to the introducer sheath 600 during introduction or insertion into tissue. The tip of the tapered portion 680 allows for easy entry through the skin into the subclavian or cephalic vein. By pressing the knob 670 against the handle 630, the dilator 660 may be fully inserted into the introducer sheath 600. Full insertion of the dilator 660 is realized when the handle 630 meets and stops the knob 670 from further penetration into the introducer sheath 600. When fully inserted inside the introducer sheath 600, a length of about 1-10 cm of the dilator 660 remains extended through and out of the introducer sheath 600.

FIG. 7 is a perspective view of the anterior portion of the heart 100 showing the lead 300 inserted in the coronary sinus region. Prior to inserting the lead 300 into the heart 100, the introducer sheath 600 may be used to facilitate insertion of the lead 300. In one embodiment, the method of implanting the lead 300 is as follows.

A detailed description of placing the sheath follows. Following Standard Selinger Technique, an 18-gauge needle is inserted into a vein (subclavian or cephalic). A J-tipped guidewire 682 (FIG. 6C) is placed into the needle (not shown) and then is placed into the vein through the needle. The needle is then removed over the guidewire. The dilator 660, while located within the introducer 600 (FIG. 6C), is pushed over the J-tipped guidewire 682 through the tissue and ultimately into the vein and finally into the superior vena cava 170 (FIG. 7). At this point, the dilator 660 and the J-tipped guidewire are pulled out of the introducer 600. The open end of the introducer 600 is then placed in the right atrium near the coronary sinus OS (190). Next the lead 300 is placed through the introducer 600 into the coronary sinus OS (190). Now the introducer 600 can be inserted into the coronary sinus (OS) (190). This provides a conduit for facilitating and supporting the placement of the lead 300 in the coronary sinus and ultimately into the more distal cardiac veins.

The stylet 200 is inserted into the lead 300 as illustrated in FIGS. 3B-3D above. The stylet 200 is used to direct the lead 300 into the introducer sheath 600 by sliding the lead 300 along the main body 610, until the distal portion of the lead 300 reaches inside the coronary sinus vein 110. The combination of the stylet 200 and introducer sheath 600 in this configuration provides support to and aids in preventing bulging of the lead 300 during initial placement of the lead into the coronary sinus vein 110. In some cases, a stylet (not shown in this figure) having dimensions greater than the stylet 200 may be used to guide the lead through the introducer sheath 600 until the lead 300 reaches the coronary sinus vein 110. For instance, the diameter of the proximal portion of the thick stylet may be about 0.020, but other stylets having a diameter in the range of about 0.015-0.030 with a shorter length taper may be used.

As noted above, the stylet 200 is used to guide the lead 300 through the os 190 into the coronary sinus vein 110. As shown in FIG. 7, to penetrate through the os 190, the lead 300 may undergo one or more relatively sharp or tortuous turns. Depending on the application, placing at least a portion of the distal portion 320 in the coronary sinus vein 110 may be desirable. It may also be desirable to place the distal portion 320 inside another vessel, such as the great cardiac vein 120, left marginal vein 130, middle cardiac vein 150, or the small cardiac vein 160 (see FIG. 1). Generally, the placement site of the distal portion 320 indicates the chamber of the heart, which is to be monitored or stimulated. In this embodiment, it is desirable to place at least a portion of the distal portion 320 inside the LPV vein 140 to allow sensing, pacing, and/or cardioversion-defibrillation of the left ventricle.

When the distal portion 320 reaches the opening of the LPV vein 140, the stylet 200 is manipulated to guide the lead 300 to enter into the LPV vein 140. In manipulating the stylet 200, the clinician may have to pull the stylet 200 out of the lead 300 until the distal tip of the stylet reaches just below or above the first bend 312, so as to steer the tip of the lead 300 into the opening of the LPV vein 140. Once the tip of the lead 300 is steered into the LPV vein 140, the stylet 200 may be pushed back into the lead 300 to substantially fully straighten at least a portion of the distal portion 320 as illustrated in FIG. 3C. Hence, in a way the bends 312 and 314 also aid in steering the lead 300 while maneuvering through tortuous coronary vessels. Once at least a portion of the distal portion 320 is inside the LPV vein 140, the stylet 200 is carefully removed or withdrawn from the lead 200, so as to maintain the distal portion 320 in its desired position. The tapered portion 220 allows removal of the stylet 200 with substantially no dragging or dislodgment of the distal portion 320. Accordingly, the lead 300 remains substantially in its placement site inside the coronary sinus region.

As shown in FIG. 7, once the stylet 200 is removed from the distal portion 320, the two or more bends 312 and 314 re-appear inside the LPV vein 140. As noted above, the friction forces or bias, created between the bends (312 and 314) and the inner wall of the coronary vessel, aid in keeping the lead 300 in its place inside the LPV 140. Hence, the removal of the stylet 200 from the lead 300 does not cause dislodgment or displacement of the lead 300. Finally, the introducer sheath 600 may be removed from the os 190 and right atrium while keeping the lead 300 inside the coronary sinus region. With the lead 300 in its place, a cardiac device, such as a pacemaker and/or ICD may be connected to the lead 300 to perform cardiac pacing, sensing, and/or cardioversion-defibrillation in the coronary sinus region using the ring electrode 340 and/or tip electrode 330.

FIG. 8 is a perspective view of the anterior portion of the heart illustrating another embodiment of the lead system inserted in the coronary sinus vein 110. As shown in FIG. 8, in this embodiment the guidewire 410 is used to guide the lead 500 into the coronary sinus vein 110. Prior to inserting the lead 500 into the heart 100, it may be desirable to insert the introducer sheath 600 into the right atrium 180 and pass the tapered portion 620 through the os 190 as fully described in FIG. 7. Once the introducer sheath 600 is in place, the guidewire 410 is inserted into the introducer sheath 600 along the main body 610 until the guidewire is inside the coronary sinus vein 110. The guidewire 410 may be further advanced and maneuvered in the coronary sinus vein 110 until the guidewire 410 reaches a desired vessel (e.g., LPV vein 140) for placing the lead 500. Subsequently, the lead 500 may be slid over the guidewire 410 through its opening 428 in the distal portion 416. The lead 500 may be advanced inside the introducer sheath 600 until at least a portion of the lead 500 is inside the coronary sinus vein 110 as shown in FIG. 8. While keeping the guidewire 410 in a desired location (e.g., the LPV vein 140), the lead 500 may be further advanced along the guidewire 410 for placement in the LPV vein 140. After placement of the lead 500, the guidewire 410 is withdrawn from the lead 500 whereafter the lead 500 retains its original shape having two or more bends as illustrated in FIG. 7. As noted above, the introducer sheath 600 may thereafter be removed from the right atrium 180.

Figure 9:
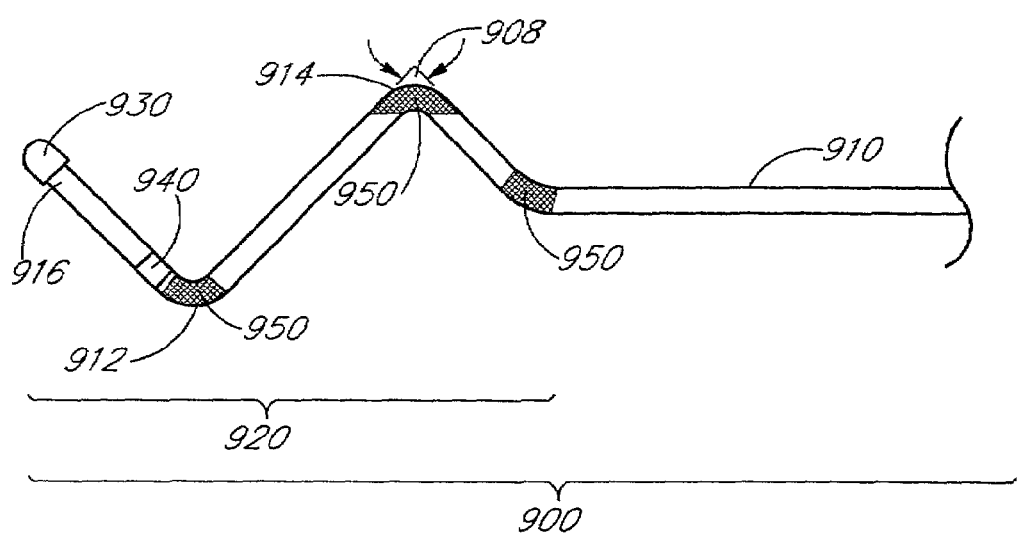
FIG. 9 is a longitudinal view of a fourth embodiment of the lead having one or more roughened regions.

In another embodiment, the invention provides a lead 900 which passively anchors itself inside coronary vessels, such as the coronary sinus vein, great cardiac vein, left marginal vein, left posterior ventricular vein, or small cardiac vein or any other vein which feeds into the coronary sinus. FIG. 9 shows an exemplary lead 900 in accordance with this embodiment of the invention. The lead 900 may comprise the lead 300, lead 400, or lead 500, which are described above. Alternatively, the lead 900 may comprise any other lead, which is suitable for placement in coronary vessels and, particularly, the coronary sinus region. Accordingly, as shown in FIG. 9, the lead 900 comprises a main body 910 connected to a distal portion 920. The distal portion 920 includes a tip 916, first bend 912, and second bend 914. The lead 900 may further comprise a tip electrode 930 connected to the tip 916, and a ring electrode 940 connected to the distal portion 920, between the tip 916 and first bend 912 or any location proximal to tip electrode.

In this embodiment, it is desirable to have the lead 900 include one or more regions 950 which are textured, or roughened, at strategically selected locations on the external surface of the lead 900. The textured regions 950 aid to fixate the lead 900 inside the coronary sinus region. It is particularly desirable to locate the textured regions 950 on the external surface of the distal portion 920 to prevent its dislodgment or displacement inside the coronary sinus region. For instance, the textured regions 950 may be located on, before, or after the first bend 912, second bend 914, and/or therebetween on the external surface of the distal portion 920. The textured regions 950 create or emphasize friction forces between the external surface of the lead 900 and the inner wall of the vessel, e.g., the LPV vein 140. Moreover, in view of the relatively low flow of blood in the coronary sinus region, intravascular material such as cells, tissue and/or proteins are likely to penetrate into and intertwine with the textured regions 950. This intertwining enhances the strength of the friction forces, thereby causing the lead 900 to fixate itself inside the coronary sinus region.

The textured regions 950 may be created using a soda-blasting technique which roughens desired portions of the insulation tubing of the lead 900. Soda-blasting is a technique which uses sodium bicarbonate (non-toxic and water-soluble compound) to create a roughened texture on a surface a material, such as the insulation tubing of the lead 900. A specialized blasting instrument may use compressed air to propel sodium bicarbonate particles onto the desired surface of the lead 900. Upon striking the surface of the lead 900, the propelled sodium bicarbonate particles etches the surface, thereby creating or emphasizing the roughened texture on the surface of the lead 900. The size of the surface area to be roughened may be controlled using blasting nozzle heads having various sizes, which are known in the art.

In another embodiment, the textured regions 950 may be created by applying any biocompatible porous material, such as expanded polytetrafluoroethylene (ePTFE), onto desired areas of the surface of the lead 900. An ePTFE layer typically comprises a microstructure of nodes or pores interconnected by fibrils. The size of a pore may be of any size which is suitable for allowing penetration or intertwining of cells or tissue with the pores of the ePTFE layer. For example, in this embodiment, the size of a pore may be greater than 4 microns. As indicated above, the ePTFE may be layered onto the external surface of the lead 900 in strategic locations of the distal portion 920. The thickness of the ePTFE layer typically depends on the size of the lead 900 and coronary sinus veins. For example, the thickness of the ePTFE layer may be in the range of about 0.5-2.0 millimeters. There are several publications in the art which describe how to apply or make porous ePTFE layers or tubings. For further information on the method of making porous ePTFE, reference is made to U.S. Pat. No. 4,082,893 issued to Okita et al. which is incorporated by reference.

In another embodiment, the textured regions 950 may be generated using a crimp mold having a desired surface texture. As noted above, the insulation tubing of the lead 900 may comprise any flexible implantable material, such as silicone or polyurethane. Creating the textured surface on the insulation tubing may occur during the curing process of the insulation tubing. For example, a Q7-4780 rubber may be partially cured by passing it through a heater or oven having a temperature of about 370 degrees centigrade for a period of few seconds. The partially cured rubber is then placed in a crimp mold having the desired geometric shape (e.g., same as the shape of the lead 300, 400, or 500). The crimp mold shapes the lead 900 to have a desired number of bends. Moreover, the crimp mold preferably includes the desired surface texture to produce a textured surface in selected regions on the external surface of the lead 900, as illustrated in FIG. 9. The rubber may then be fully cured by placing it in an oven having a temperature in the range of about 115-150 degrees centigrade for about 2 hours. After the rubber cools down, the rubber possesses the geometric characteristics of the lead 900 including the textured regions 950.

In view of the foregoing, it will be appreciated that the invention overcomes the long-standing need for a lead system which may be implanted in difficult-to-reach regions of the heart, such as the coronary sinus region and tributary veins. The invention provides a lead system which is implantable in the coronary sinus region of a human heart, without experiencing displacement or dislodgment. The invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes, which fall within the meaning and range of equivalency of the claims, are to be embraced within their scope.

What is claimed is:

1. An implantable stimulation lead system comprising:
    at least one electrode;
    a lead body connected to the at least one electrode, the lead body including at least a distal portion having at least two non-helical bends dimensioned to passively anchor the distal portion of the lead body in a coronary vein overlying a left ventricle;
    wherein the at least two non-helical bends define substantially an s-shaped portion so as to bias the at least two non-helical bends against sides of a vessel wall of the coronary vein; and
    wherein the at least one electrode located on one of the at least two non-helical bends so that the at least one electrode is adapted to electrically couple to one of the sides of the vessel wall of the coronary vein.

2. The lead system, as defined in claim 1, wherein the lead body has a lumen therethrough, the lead system further comprising:
    a stylet disposed and slidably movable within the lumen, wherein:
    when the stylet is partially withdrawn, the s-shaped portion forms a steerable canted end; and
    when the stylet is fully withdrawn, the s-shaped portion passively anchors in a desired position.

3. The lead system, as defined in claim 2, wherein the stylet comprises a tapered portion which aids in tracking the coronary sinus.

4. The lead system, as defined in claim 2, further comprising a tip electrode; and wherein the steerable canted end orients the tip electrode toward the vessel wall of the coronary vein.

5. The lead system, as defined in claim 2, wherein the at least two non-helical bends are dimensioned to passively anchor the lead in one of the coronary sinus vein, great cardiac vein, left marginal vein, left posterior ventricular vein, and small cardiac vein.

6. The lead system, as recited in claim 5, wherein the at least two non-helical bends comprises a first bend located in the range of 0.15-0.7 inches from a distal end of the lead body.

7. The lead system, as recited in claim 6, wherein the at least two non-helical bends comprises a second bend located in the range of 0.15-0.7 inches from the first bend.

8. The lead system, as recited in claim 5, wherein the non-helical bends are substantially in the same geometric plane.

9. The lead system, as recited in claim 5, wherein the non-helical bends are substantially in different geometric planes.

10. The lead system, as defined in claim 1, wherein the at least one electrode comprises a ring electrode.

11. The lead system, as defined in claim 1, wherein the non-helical bends comprise two sides forming an angle in the range of about 30-150 degrees.

12. The lead system, as recited in claim 1, further comprising a plurality of bends substantially in the same geometric plane.

13. The lead system, as recited in claim 1, further comprising a plurality of bends substantially in a different geometric plane.

14. The lead system, as defined in claim 1, wherein the lead body comprises a distal opening configured to receive a guidewire and allow the lead body to slide over the guidewire.

15. The lead system, as defined in claim 1, wherein the lead body comprises an insulation layer having at least one textured region positioned on the surface of the insulation layer, the at least one textured region having increased surface area which passively anchors the lead body inside the coronary sinus.

16. The lead system, as defined in claim 15, wherein the at least one textured region comprises a layer of expanded polytetrafluoroethylene (ePTFE).

17. The lead system, as defined in claim 15, wherein the at least one textured region comprises a layer of porous material having a plurality of pores, each of the plurality of pores being dimensioned to allow the penetration and growth of intravascular material therein.

18. The lead system, as defined in claim 1, wherein the lead body is adapted for placement by a guidewire and a stylet to place the distal portion in the coronary vein.

19. The lead, as recited in claim 1, wherein:
the two bends have a peak-to-peak amplitude that is greater than a target vessel in the coronary sinus region;
whereby the vessel exerts a force to compress the two bends so that a sufficient bias is exerted for securing the lead.

* * * * *